United States Patent [19]

Yamamoto et al.

[11] Patent Number: 4,794,124

[45] Date of Patent: Dec. 27, 1988

[54] THERAPEUTIC COMPOSITION FOR DIABETIC COMPLICATIONS

[75] Inventors: Yujiro Yamamoto, Suita; Hiroshi Kuriyama, Toyonaka; Mitsuyoshi Azuma, Amagasaki, all of Japan

[73] Assignee: Senju Pharmaceutical Co., Ltd., Osaka, Japan

[21] Appl. No.: 929,305

[22] Filed: Nov. 12, 1986

[30] Foreign Application Priority Data

Nov. 27, 1985 [JP] Japan .................................. 60-268065

[51] Int. Cl.$^4$ ............................................. A61K 37/44
[52] U.S. Cl. ..................................... 514/562; 514/912
[58] Field of Search ................................ 514/562, 912

[56] References Cited

U.S. PATENT DOCUMENTS 4,002,758 1/1977 Bigou .................................. 514/912
4,665,082 5/1987 Meister et al. ...................... 514/562

FOREIGN PATENT DOCUMENTS 2441621 3/1976 Fed. Rep. of Germany ...... 514/562
55-92315 7/1980 Japan .................................. 514/562

OTHER PUBLICATIONS

Ocular Pharmacology 4th ed.—1978 pp. 528-529—The C. V. Mosby Co.
Chem. Abst. 85:91666r (1976)—Takemoto et al.
Chem. Abst. 96:205,341r (1982)—Zhang et al.
Chem. Abst. 96 205,410r (1982)—Senju Pharm. Co. Ltd.
Yakugaku Zasshi, 89 (4), 565-578 (1969).
Yakugaku Zasshi, 89 (4) 572-578 (1969)

*Primary Examiner*—Douglas W. Robinson
*Attorney, Agent, or Firm*—Armstrong, Nikaido, Marmelstein & Kubovcik

[57] ABSTRACT

A pharmaceutical composition containing cysteine or a pharmacologically acceptable salt thereof is an effective therapeutic agent for diabetic complications, typically diabetic cataract.

1 Claim, 1 Drawing Sheet

THERAPEUTIC COMPOSITION FOR DIABETIC COMPLICATIONS

BACKGROUND OF THE INVENTION

1. Field of the Invention

The present invention relates to a pharmaceutical composition for diabetic complications. More particularly, the invention relates to a therapeutic composition adapted to effectively inhibit progression of diabetic cataract.

Patients who have had diabetes for several years may develop various diabetic complications. The most typical diabetic complications are cataract, retinopathy, nephropathy and neuropathy, and these complications occur at times even while the patients are kept under adequate blood glucose control, leading to blindness due to cataract or retinopathy, progress of nephropathy to renal failure which calls for hemodialysis treatment, peripheral neuroparalysis due to neuropathy or other serious outcomes in some cases. Heretofore, certain amino acid derivatives have been reported to be effective in the treatment of diabetes, arteriosclerosis and cataract or as a liquefying expectorant.

2. Description of the Prior Art

For example, Japanese Patent Laid-Open Application Kokai No. 52-91823 teaches the use of N-(2-mercapto-substituted acyl) amino acid amides as antidiabetic agents or therapeutic agents for artorioslerosis. Japanese Patent Laid-Open Application Kokai No. 52-111572 teaches the use of N-(mercapto-substituted acyl)histidines as therapeutic agents for arteriosclerosis. Japanese Patent Laid-Open Application Kokai No. 55-92315 describes the use of 3-mercaptopropionyl-L-cysteine as a therapeutic agent for cataract. Japanese Patent Laid-Open Application Kokai No. 55-124716 describes the use of methylmethionine sulfonium salts as therapeutic and prophylactic agents for arteriosclerotic heart disease and cerebral diseases. Japanese Patent LaidOpen Application Kokai No. 56-147715 teaches the use of N-acetylcysteine as a therapeutic agent for cataract. Japanese Patent Laid-Open Application Kokai No. 57-209214 teaches the use of cysteine as a therapeutic agent for heavy metal poisoning. Japanese Patent Laid-Open Application Kokai No. 58-88351 describes the use of acylcysteine derivatives as liquefying expectorants and antirheumatic agents. Further, Japanese Patent LaidOpen Application Kokai No. 58-208218 describes the use of a mixture of amino acids such as L-lysine, an amino acid precursor protein, carbohydrates, fats, minerals and vitamins as antidiabetic agents.

However, there is no report on the use of a highly safe protein-constituting amino acid as such in the treatment of diabetic complications, particularly as a therapeutic agent for the treatment of diabetic cataract.

The present inventors early focused attention on cysteine which is a constituent amino acid of glutathione which is known to be essential to the maintenance of crystalline lens transparency and conducted a series of studies on the pharmacologic effects of this amino acid. The studies led to the finding that cysteine has a very remarkable therapeutic effect on diabetic complications and particularly on diabetic cataract. The present invention is predicated on the above finding.

It is, therefore, an object of the present invention to provide a therapeutic composition for diabetic complications. It is another object of the present invention to provide a highly safe and effective pharmaceutical composition for the treatment of diabetic cataract.

SUMMARY OF THE INVENTION

The present invention is concerned with a pharmaceutical composition for diabetic complications which contains cysteine or a pharmacologically acceptable salt thereof as an active component.

DETAILED DESCRIPTION OF THE INVENTION

Figure 1:
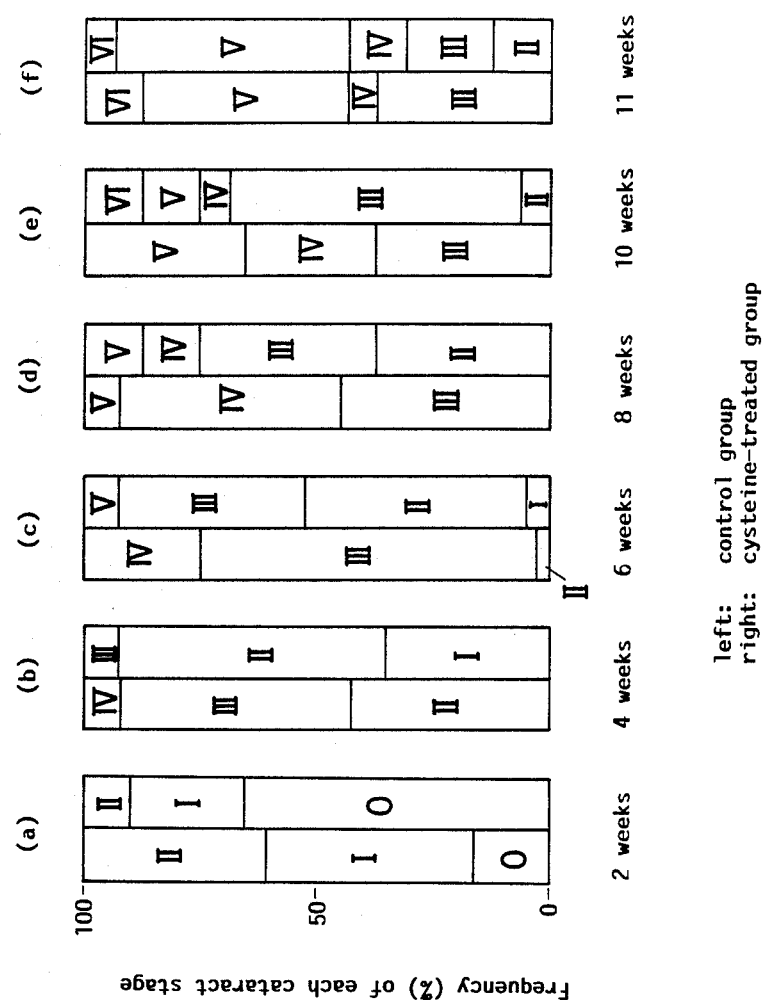
FIG. 1 is a diagrammatic representation showing the progression of cataract as bar graphs.

The pathogenesis of diabetic complications has been explained in terms of accumulation of sorbitol produced on reduction of glucose by aldose reductase in the affected tissue, and this theory has been substantiated by the prevention or inhibition of these complications by aldose reductase inhibitors. However, the pathology of diabetic complications is not as simple as permits a generalized explanation in terms of the accumulation of sorbitol in the tissue involved but much remains yet to be elucidated. The oral administration of cysteine, the active component of the therapeutic composition according to the present invention, to diabetic animals not only produces improvements in diabetes-associated metabolic disorders but also produces excellent effects against cataract which is one of diabetic complications. However, as this cysteine treatment does not inhibit accumulation of sorbitol in the tissue, the efficacy of cysteine in diabetic complications appears to come through a mechanism of action distinct from the mechanism involving the inhibition of aldose reductase.

Cysteine used as the active component of the pharmaceutical composition according to the present invention may be the free compound or a pharmacologically acceptable salt thereof. Examples of such salt include the hydrochloride, sulfate, oxalate, citrate, tartarate, lactate, alkali metal salts, ammonium salts and so on. The method of administration, dosage and toxicity of the pharmaceutical composition of the present invention are described below.

METHOD OF ADMINISTRATION

The pharmaceutical composition according to the present invention is generally administered orally in such dosage forms as tablets, capsules, granules, powders, solutions and so on. It can be administered by other routes as well; for example subcutaneously, intramuscularly or intravenously. Further, if desired, it may be used as suppositories or eye-drops.

In the forms of tablets, capsules, etc., the therapeutic composition according to the present invention may contain the common excipients such as binders (e.g. gelatin, gum arabic, gum tragacanth, polyvinylpyrrolidone, etc.), vehicles (e.g. lactose, corn starch, calcium phosphate, etc.), lubricants (e.g. magnesium stearate, polyethylene glycol, talc, silica, etc.), disintegrators (e.g. potato starch, etc.), and wetting agents such as sodium laurylsulfate and so on. When formulated as liquid preparations inclusive of parenteral products, the therapeutic composition according to the present invention may contain suspending agents, emulsifying agents, nonaqueous vehicles, preservatives, stabilizers and other additives known in pharmaceutical practice.

Dosage

The dosage depends on the patient's age and condition, the route of administration and other conditions, but the daily adult dose for oral administration may range from 10 to 5000 mg, preferably 30 to 2000 mg, and for parenteral administration may range from 10 to 5000 mg, preferably 30 to 1000 mg, given in a single dose or in divided doses. Diabetic complications usually call for prolonged pharmacotherapy but since cysteine is low in toxicity as described hereinafter, the pharmaceutical composition according to the present invention can be repeatedly administered on a long-term basis.

Acute Toxicity

The oral, intraperitoneal and subcutaneous $LD_{50}$ values of cysteine in rats are as follows.

| Species | Route of administration | Sex | $LD_{50}$ (g/kg) | Confidence limits (g/kg) |
|---|---|---|---|---|
| Rat | Oral | Male | 6.35 | 5.87–6.98 |
|  |  | Female | 5.58 | 5.00–6.17 |
|  | Intraperitoneal | Male | 1.63 | 1.46–1.82 |
|  |  | Female | 1.62 | 1.46–1.80 |
|  | Subcutaneous | Male | 1.70 | 1.60–1.80 |
|  |  | Female | 1.55 | 1.21–1.91 |

The pharmaceutical composition according to the present invention is of value in the treatment of diabetic complications and particularly in arresting progression of diabetic cataract. This therapeutic composition has an additional advantage that its active component is cysteine which is a highly safe constituent amino acid of glutathione.

EXAMPLE

The effects of oral administration of cysteine in diabetic rats were investigated.

Method

Using male SD rats weighing about 100 g, experimental diabetes was induced by injecting 70 mg/kg of streptozotocin into the caudal vein.

The rats were divided into 2 groups of 10 individuals. A first group of rats were given a 10% aqueous solution of cysteine in a volume of 0.2 ml/100 g body weight twice daily (cysteine 400 mg/kg/day) by gastric gavage beginning the day before administration of streptozotocin. This group is referred to as the cysteine-treated group. A second group received tap water similarly. This group is referred to as the control group.

Blood glucose was determined 2 days and 11 weeks after administration of streptozotocin to confirm that the rats were in hyperglycemic condition. Further, body weight was determined periodically during the study period. After 11 weeks, the blood was withdrawn from the abdominal aorta for clinical serum chemical examination. Moreover, to monitor the cataract supervening in diabetes, the rat crystalline lens was periodically examined using a slit lamp.

The progression of cataract was evaluated on the scale of the following 7 stages up to mature cataract.
0: No lens opacity at all
I: Slight opacity of the lens epithelium or small vacuoles in the equatorial region.
II: Vacuoles multiplying and merging to spread into the cortex.
III: The vacuoles pervading most of the cortex have begun to disappear.
IV: The majority of vacuoles have disappeared and the whole cortex is translucent.
V: Opacity of the lens nucleus.
VI: Opacity of the whole lens (mature cataract)

Results

The blood glucose levels in rats after 2 days and 11 weeks are shown in Table 1.

The rat blood glucose had already increased by 2 days after administration of streptozotocin and this hyperglycemic condition persisted throughout the 11-week period.

TABLE 1

| | (Blood glucose) | |
|---|---|---|
| | Control group | Cysteine-treated group |
| After 2 days | 521 ± 78 | 559 ± 99 |
| After 11 weeks | 721 ± 75 | 767 ± 77 |

(Note)
*n = 8–10
*Unit: mg/dl
*The value for normal rats = 220 ± 20 mg/dl

The time course of rat body weight is shown in Table 2.

Throughout the study period, there was no difference in rat body weight between the cysteine-treated group and the control group. Thus, the long-term repeated administration of cysteine 400 mg/kg/day did not affect the body weight gain in diabetic rats.

TABLE 2

| | (Time course of rat body weight) | |
|---|---|---|
| | Control group | Cysteine-treated group |
| After 0 day | 132 ± 7 | 130 ± 7 |
| After 19 days | 163 ± 23 | 163 ± 28 |
| After 40 days | 166 ± 30 | 167 ± 42 |
| After 54 days | 152 ± 31 | 175 ± 45 |
| After 79 days | 153 ± 43 | 177 ± 57 |

(Note)
*n = 8–10
*Unit: g

Table 3 shows the clinical serum chemistry values at week 11 after administration of streptozotocin.

The serum chemical examination performed after 11 weeks revealed that animals in the control group showed deviations from normal values in many parameters including not only those related to glycometabolism represented by serum glucose but also those related to lipid metabolism such as total cholesterol, neutral lipid, lipid peroxide, β-lipoprotein, etc., liver function-related parameters such as GOT, GPT, ALP, TTTC (thymol turbidity test), ZST (zinc sulfate test), γ-GTP, LAP, total bilirubin, etc. and some kidney function parameters such as uric acid. Thus, it was evident that the general metabolic functions were suppressed in these diabetic rats.

On the other hand, the animals in the cysteinetreated group showed serum chemical parameters close to the normal values, indicating that the metabolic functional abnormalities due to diabetes had been improved by the oral administration of cysteine.

TABLE 3

|  |  | Normal | Control group | Cysteine-treated group |
|---|---|---|---|---|
| Total cholesterol | (mg/dl) | 51 ± 6 | 175 ± 76 | 118 ± 57 |
| Neutral lipid | (mg/dl) | 90 ± 25 | 1437 ± 858 | 645 ± 605 |
| Lipid peroxide | (nmol/dl) | 3.95 ± 0.53 | 5.40 ± 0.68 | 4.48 ± 0.56 |
| β-lipo-protein | (mg/dl) | 112 ± 13 | 493 ± 233 | 299 ± 173 |
| GOT | (U/L) | 102 ± 42 | 952 ± 1038 | 495 ± 358 |
| GPT | (U/L) | 61 ± 27 | 450 ± 320 | 311 ± 184 |
| ALP | (KAU) | 48 ± 8 | 83 ± 25 | 68 ± 26 |
| γ-GTP | (U/L) | 2.4 ± 2.0 | 42.9 ± 31.3 | 13.4 ± 7.2 |
| LAP | (GRU) | 199 ± 15 | 297 ± 78 | 234 ± 66 |
| Total bilirubin | (mg/dl) | 0.2 ± 0.0 | 0.43 ± 0.23 | 0.28 ± 0.18 |
| TTT | (U) | 0.15 ± 0.05 | 3.94 ± 3.88 | 1.03 ± 0.90 |
| ZST | (U) | 1.2 ± 0.1 | 6.2 ± 4.8 | 2.6 ± 1.3 |
| Uric acid | (mg/dl) | 1.8 ± 0.4 | 2.5 ± 2.5 | 1.5 ± 0.5 | n = 8-10

Then, cataract which is a diabetic complication ready to develop in such diabetic animal models was studied by monitoring the rats for 11 weeks.

The bar graphs in FIG. 1(a) through (f) show the time course of cataract stages. The bar graph (a) represents the condition after 2 weeks, (b) the condition after 4 weeks, (c) the condition after 6 weeks, (d) the condition after 8 weeks, (e) the condition after 10 weeks, and (f) the condition after 11 weeks. The bar at left stands for the control group and the bar at right stands for the cysteine-treated group. In each graph, the vertical axis represents the frequency (%) of each cataract stage during each observation period. (See FIG. 1.)

It will be apparent from FIG. 1 that in any observation period, the progress of cataract was inhibited in the cysteine-treated group as compared with the control group. Cumulative variance analysis of these result indicated a significant retarding effect on the progression of cataract in the cysteinetreated group ($p < 0.0001$).

In order to examine whether the above effect of cysteine against diabetic cataract was due to inhibition of accumulation of sorbitol in the lens, a further experiment was performed in a similar design, in which the rats were sacrificed 2 and 3 weeks after administration of streptozotooin and the sorbitol content of the lens was determined. The results are shown in Table 4.

There was no significant difference between the control group and the cysteine-treated group as to accumulation of sorbitol in the lens.

TABLE 4

(Sorbitol content of the lens)

|  | Control group | Cysteine-treated group |
|---|---|---|
| After 2 weeks | 0.996 ± 0.286 | 1.056 ± 0.166 |
| After 3 weeks | 1.186 ± 0.164 | 1.025 ± 0.031 |

(note)
*Unit: μmole/lens
n = 4-5
*Normal rage = 0.005 ± 0.026 μmole/lens

Since the oral administration of cysteine produced improvements in general metabolic functions in diabetic animals as is seen from the serum chemistry values, the oral treatment with cysteine is evident to be effective not only in the treatment of cataract but also in the treatment of other diabetic complications such as retinopathy, nephropathy and neuropathy.

EXAMPLE 1 (TABLETS FOR ORAL ADMINISTRATION)

Using the following components, tablets for oral administration were manufactured by the established pharmaceutical procedure.

|  | (per tablet) |
|---|---|
| Cysteine | 100 mg |
| Lactose | 80 mg |
| Corn starch | 20 mg |
| Magnesium stearate | 3 mg |

EXAMPLE 2 (GRANULES)

Using the following components, granules were manufactured by the established pharmaceutical procedure.

| Cysteine | 100 mg |
|---|---|
| Polyvinylpyrrolidone | 30 mg |
| Lactose | 300 mg |
| Silica | 15 mg |

EXAMPLE 3 (CAPSULES)

The following components were mixed and filled into an ampule in accordance with the established pharmaceutical procedure.

| Cysteine | 100 mg |
|---|---|
| Crystalline cellulose | 50 mg |
| Lactose | 50 mg |
| Talc | 5 mg |

EXAMPLE 4 (INJECTIONS)

| Cysteine | 100 mg |
|---|---|
| Sodium chloride | 20 mg |

Provided as a two-package preparation. The components are extemporaneously dissolved in 5 cc of distilled water. The solution has a pH value of 5.2 and an osmotic pressure of 286 m Osm/kg.

What is claimed is:

1. A method of inhibiting the formation of cataracts in a diabetic animal which comprises orally administering to the animal 10-5000 mg per day of cysteine or a pharmacologically acceptable salt thereof.

* * * * *